(12) United States Patent
Öhrlein et al.

(10) Patent No.: US 7,504,532 B2
(45) Date of Patent: Mar. 17, 2009

(54) PROCESS FOR THE PREPARATION OF 7-AMINO SYN 3,5-DIHYDROXY HEPTANOIC ACID DERIVATIVES, INTERMEDIATES THEREOF AND METHODS FOR THEIR PREPARATION

(75) Inventors: Reinhold Öhrlein, Rheinfelden-Herten (DE); Gabriele Baisch, Baselstrasse (DE); Hans Jörg Kirner, Pratteln (CH); Stephan Burkhardt, Gelterkinden (CH); Martin Studer, Basel (CH); Frank Bienewald, Hegenheim (FR)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 11/941,347

(22) Filed: Nov. 16, 2007

(65) Prior Publication Data
US 2008/0125601 A1    May 29, 2008

Related U.S. Application Data

(62) Division of application No. 10/482,946, filed as application No. PCT/EP02/07308 on Jul. 2, 2002, now Pat. No. 7,317,123.

(30) Foreign Application Priority Data
Jul. 6, 2001   (EP) ............................ 01810678038

(51) Int. Cl.
C07C 229/00   (2006.01)
C07C 291/00   (2006.01)
C07C 59/10    (2006.01)

(52) U.S. Cl. .......................... 560/170; 562/567; 562/587
(58) Field of Classification Search ........................ None
See application file for complete search history.

(56) References Cited

U.S. PATENT DOCUMENTS

| | | | |
|---|---|---|---|
| 5,003,008 A | | 3/1991 | Kobayashi |
| 5,051,502 A | * | 9/1991 | Miller et al. ................. 540/205 |
| 5,097,045 A | | 3/1992 | Butler et al. |
| 5,248,793 A | | 9/1993 | Millar et al. |
| 5,510,488 A | | 4/1996 | Butler et al. |
| 5,599,954 A | | 2/1997 | Mitsuhashi et al. |
| 6,596,879 B2 | | 7/2003 | Bosch et al. |

FOREIGN PATENT DOCUMENTS

| | | |
|---|---|---|
| EP | 0352864 | 1/1990 |
| EP | 0385733 | 9/1990 |
| EP | 0436851 | 7/1991 |
| WO | WO 89/07598 A2 | 8/1989 |
| WO | WO 93/07115 A1 | 4/1993 |
| WO | WO 9932434 | 7/1999 |
| WO | WO 00/68211 | 11/2000 |

OTHER PUBLICATIONS

Beilstein Database; *Beilstein Institut zur Foerderung der Chemischen Wissenschaften*, database No. XP-000608147; [K. L. Baumann, et al., *The Convergent Synthesis of CI-981, An Optically Active, Highly Posue Selective Inhibitor of HMG-COA Reductase*, Tetrahedron Letters, vol. 33, No. 17, pp. 2283-2284, 1992].
Beilstein Database; *Beilstein Institut zur Foerderung der Chemischen Wissenschaften*, Beilstein database No. XP-002218019; [Matthew A. Williams, Marvin J. Miller, and Nigam P. Rath, *Hemiketal Formation and Subsequent Intramolecular Acylation of an N-Hydroxy β-Lactam*, J. Org. Chem. 1991, vol. 56, No. 3, pp. 1293-1296].
Beilstein Database; *Beilstein Institut zur Foerderung der Chemischen Wissenschaften*, Beilstein database No. XP-002218024; Beilstein Registry No. 6374676; 3 pages;.
Beilstein Database; *Beilstein Institut zur Foerderung der Chemischen Wissenschaften*, Beilstein database No. XP-002218023; Beilstein Registry No. 3567301; 2 pages; [J. Monteiro, J. Braun, and F. Le Goffic, Synth. Commun. 1990, vol. 20, No. 3, pp. 315-319].
Beilstein Database; *Beilstein Institut zur Foerderung der Chemischen Wissenschaften*, Beilstein database No. XP-002218022; Beilstein Registry No. 2261529; 1 page; [T. Rosen, M. Watanabe, and C. Heathcock, J. Org. Chem. 1984, vol. 49, No. 19, pp. 3657-3659].
Beilstein Database; *Beilstein Institut zur Foerderung der Chemischen Wissenschaften*, Beilstein database No. XP-002218021; Beilstein Registry No. 1962247; 1 page; [L. Novak, J. Rohaly, L. Poppe, G. Hornyanszky, P. Kolonits, et al., Liebigs Ann. Chem. 1992, vol. 2, pp. 145-158].
Beilstein Database; *Beilstein Institut zur Foerderung der Chemischen Wissenschaften*, Beilstein database No. XP-002218020; Beilstein Registry No. 4322437; 2 pages;.
Beilstein Database; *Beilstein Institut zur Foerderung der Chemischen Wissenschaften*, Beilstein database No. XP-002186065; Beilstein Registry No. 6798562; 4 pages;.
Beilstein Database; *Beilstein Institut zur Foerderung der Chemischen Wissenschaften*, database No. XP-002217821; Beilstein Registry No. 225285; 1 page.
Beilstein Database; *Beilstein Institut zur Foerderung der Chemischen Wissenschaften*, database No. XP-001038115; [D. W. Brooks, et al., *Remote Substituent Effects in Microbial Reductions of 3-Ketoglutarate and 3 Ketoadipate Esters*, Tetrahedron Letters, vol. 25, No. 41, pp. 4623-4626, 1984].

(Continued)

Primary Examiner—Karl J Puttlitz
(74) Attorney, Agent, or Firm—Kenyon & Kenyon LLP

(57) ABSTRACT

Synthesis methods for the preparation of intermediates which are suitable for the preparation of statin derivatives, and especially to synthesis methods for the intermediate of formula (VI) wherein $R_a'$ and $R_c'$ are each independently of the other hydrogen or hydroxy-protecting group, or together are a bridging hydroxy-protecting group; and $R_b$ is a carboxy-protecting group.

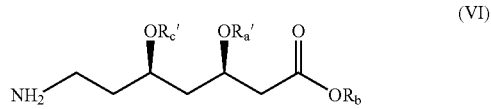

(VI)

3 Claims, No Drawings

OTHER PUBLICATIONS

Beilstein Database; *Beilstein Institut zur Foerderung der Chemischen Wissenschaften*, database No. XP-001038113;[R. Roy, et al., *Chemenzymatic Synthesis of A C5-Chiral Building Block: A Substrate Modification Approach*, Tetrahedron Letters, vol. 28, No. 42, pp. 4935-4938, 1987].

J. F. W. McOmie, *Protective Groups in Organic Chemistry*, Plenum Press, London and New York, 1973.

T. W. Greene and P. G. M. Wuts, *Protective Groups in Organic Synthesis*, Third Edition, Wiley, New York 1999.

Jochen Lehmann, *Chemie der Kohlenhydrate: Monosaccharide and Derivative*, Georg Thieme Verlag, Stuttgart 1974, pp. 1-279.

H. J. Rehm, G. Reed, Biotechnology, VCH 1998, Second Edition, pp. 407-411.

Beilstein Database; Beilstein Institut zur Foerderung de Chemischen Wissenschaften, Beilstein database No. XP-002199750.

Beilstein Database; Beilstein Institut zur Foerderung de Chemischen Wissenschaften, database No. XP-002186064; Beilstein Registry No. 1726574; 5 pages.

Beilstein Database; Beilstein Institut zur Foerderung der Chemischen Wissenschaften, database No. XP-000608146; [P. L. Brower, et al., The Synthesis of (4r-Cis)-1,1-Dimethylethyl 6-Cyanomethyl-2,2-Dimethyl L-1,3-Dioxane-4-Acetate, A Key Intermediate for the Preparation of CI-981, A Highly Potent, Tissue Selective Inhibitor of HMG-COA Reductase, Tetrahedron Letters, vol. 33, No. 17, pp. 2279-2282, Apr. 21, 1992].

K. Faber, *Biotransformation in Organic Chemistry*, Springer 1997, Third Edition, pp. 345-356, ISBN 3-540-61688-8.

K. Faber, *Biotransformation in Organic Chemistry*, Springer 1997, Third Edition, pp. 304-306, ISBN 3-540-61688-8.

H. J. Rehm, G. Reed, Biotechnology, VCH 1998, Second Edition, pp. 40-42.

International Search Report of Application No. PCT/EP02/07309, dated Nov. 11, 2002.

* cited by examiner

PROCESS FOR THE PREPARATION OF 7-AMINO SYN 3,5-DIHYDROXY HEPTANOIC ACID DERIVATIVES, INTERMEDIATES THEREOF AND METHODS FOR THEIR PREPARATION

CROSS-REFERENCES

This application is divisional of application Ser. No. 10/482,946 (filed 6 Jul. 2004 now U.S. Pat. No. 7,317,123), which is a 371 national phase application of PCT/EP02/07308 filed on 2 Jul. 2002, claiming priority to Application No. 01810670.8 filed on 6 Jul. 2001 in the European Patent Office. The contents of each of these applications are incorporated by reference in their entirety.

SUMMARY OF THE INVENTION

The invention relates to novel preparation processes for the preparation of 3,5-dihydroxy-heptanoic acid derivatives and to novel intermediates and processes for their preparation. The dihydroxyheptanoic acid derivatives and the intermediates are suitable for advantageous syntheses of statins.

BACKGROUND TO THE INVENTION

Statins are a class of pharmaceuticals that inhibit the enzyme hydroxymethylglutaryl CoA reductase (HMG-CoA-R) and are therefore widely used as hypolipidaemic agents and agents that lower the level of cholesterol in the blood (hypocholesterollipidaemic agents). All synthetically prepared HMG-CoA-R inhibitors have, as common structural features, an aromatic base structure and the so-called statin side chain, as symbolised by the following formula:

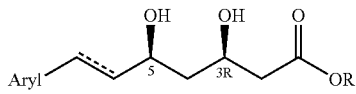

(wherein Aryl denotes aromatic, heterocyclic or aromatic-heterocyclic, unsubstituted or substituted, mono-, di- or polycyclic ring systems). Such a structural unit can be found in a whole range of pharmaceutically active agents, such as cerivastatin (Bayer AG), fluvastatin (Novartis), itavastatin (NK-104; Kowa Company Ltd.), BMY 22089 (Bristol-Myers Squibb), rosuvastatin (S-4522, AstraZeneca/Shionogi), glenvastin (Hoechst (Aventis) and atorvastatin (Warner-Lambert/Gödecke-Parke Davies/Pfizer).

The aim of the present invention is to provide new efficient methods of synthesising some known statin derivatives and to provide new intermediate compounds.

GENERAL DESCRIPTION OF THE INVENTION

Key steps in the synthesis according to the invention are early introduction of the correct absolute stereochemistry at C-3 (R) and subsequent regioselective chain lengthening. Unlike the linear synthesis processes in the prior art, the use of the novel statin side chain building blocks allows a convergent synthesis. The invention relates also to novel intermediates.

DETAILED DESCRIPTION OF THE INVENTION

The present invention concerns a process for the preparation of the intermediate of formula VI

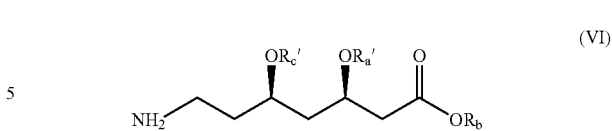

wherein $R_a'$ and $R_c'$ are each independently of the other hydrogen or a hydroxy-protecting group or together are a bridging hydroxy-protecting group, and $R_b$ is a carboxy-protecting group, which is suitable for the preparation of statin derivatives, which process is carried out by conversion of the intermediate of formula XVI

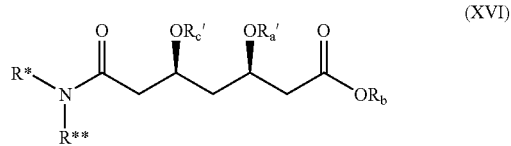

wherein $R_a'$ and $R_c'$ are each independently of the other hydrogen or a hydroxy-protecting group, R* and R** are each independently of the other hydrogen or an amide-protecting group, and $R_b$ is a carboxy-protecting group; wherein compound of formula XVI is prepared by a process which comprises the preparation of a compound of formula I

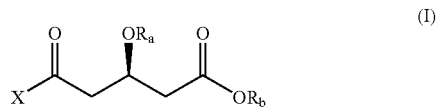

wherein X is halogen, acyloxy, activated hydrocarbyloxy, activated hydrocarbylthio or —N(CH$_3$)—OCH$_3$, $R_a$ is hydrogen or a hydroxy-protecting group and $R_b$ is a carboxy-protecting group, which intermediate converted into an amide of formula I*

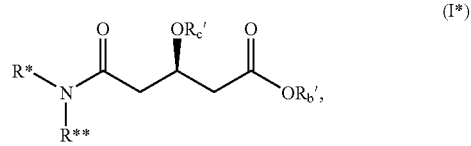

wherein $R_c'$ is hydrogen or a hydroxy-protecting group, $R_b'$ is hydrogen or a carboxy-protecting group and R* and R** are each independently of the other hydrogen or an amide-protecting group, preferably alkyl or substituted alkyl, more preferably $C_1$-$C_4$alkyl, such as methyl, ethyl, n-propyl, iso-propyl, n-butyl, tert.-butyl, sec.-butyl, or substituted alkyl, such as benzyl, most preferably benzyl, which compound can then be converted for the preparation of statin precursors, especially those of formula VI already described above:

The conversion of compound of formula I* wherein $R_c'$ is hydrogen (obtainable, if necessary, from the compound of formula I* wherein $R_c'$ is a hydroxy-protecting group, by removal of protecting groups) and $R_b'$, R* and R** are as defined for the compound of formula I*, preferably at least one of the radicals R* and R** being an amide-protecting group, is carried out by reaction in the presence of a strong base with a compound of formula XX

wherein $R_b$ is a carboxy-protecting group, to form a compound of formula XV

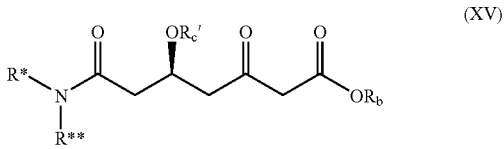

wherein R* and R** are as defined for compounds of formula I*, $R_c'$ is hydrogen and $R_b$ is a carboxy-protecting group; that compound is then reduced diastereoselectively to form a syn-diol of formula XVI

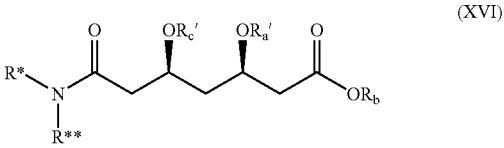

wherein $R_a'$ and $R_c'$ are hydrogen; or, after subsequent introduction of protecting groups, $R_a'$ and $R_c'$ are each independently of the other hydrogen or a hydroxy-protecting group, with the proviso that at least one of the two radicals is such a protecting group, or $R_a'$ and $R_c'$ together are a bridging hydroxy-protecting group; R* and R** are as defined for the compound of formula I*, preferably at least one of them being an amide-protecting group; and $R_b$ is a carboxy-protecting group; the resulting compound of formula XVI is then converted into a compound of formula VI, as described above, by reduction and removal of protecting groups R* and R**, if present.

The invention relates also to a process for the preparation of the compound of formula I as defined above.

For that purpose, a compound of formula XI

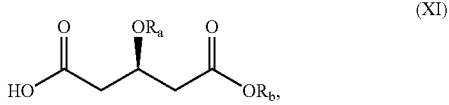

wherein $R_a$ is a hydroxy-protecting group (or, less preferred because the ee is then lower, hydrogen) and $R_b$ is a carboxy-protecting group, is converted into the corresponding compound of formula I using a reagent that introduces the radical X.

The compound of formula XI is in turn advantageously prepared by hydrolysing a compound of formula XII

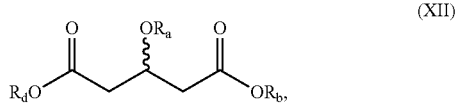

wherein $R_a$ is a hydroxy-protecting group (or, less preferred because the ee is then lower, hydrogen), $R_b$ is a carboxy-protecting group and $R_d$ is hydrocarbyl, by means of an enantioselective catalyst (preferably by hydrolysis using a biocatalyst) with the removal of the radical $R_d$, the corresponding compound of formula XI being obtained directly.

The compound of formula XII is advantageously obtained by reacting a glutaric acid derivative of formula XIII

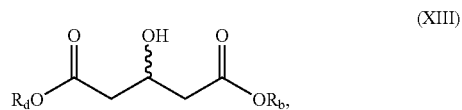

wherein $R_b$ and $R_d$ are as defined for compounds of formula XII, by introduction of a hydroxy-protecting group using the corresponding reagent suitable for the introduction of the protecting group.

The invention relates also to new individual steps of the processes described above, to new combinations of individual steps and to new intermediate compounds.

Unless indicated to the contrary, the general terms (including the reactions and reaction conditions) used hereinabove and hereinbelow preferably have the following meanings— these specific definitions and descriptions of reactions can be used independently of one another instead of the general terms mentioned hereinabove and hereinbelow, resulting in preferred embodiments of the invention:

The prefix "-lower" or "lower" indicates that the radical in question contains preferably up to 7 carbon atoms, especially up to 4 carbon atoms. Lower alkyl is therefore preferably $C_1$-$C_7$-alkyl, especially $C_1$-$C_4$alkyl, and may be unbranched or branched one or more times, insofar as possible. Unsaturated radicals, such as alkenyl or alkynyl, have at least two carbon atoms, preferably from 2 to 7, especially from 3 to 7, more especially 3 or 4.

In the processes mentioned hereinabove and hereinbelow, it is possible at any stage, even where not explicitly mentioned, for one or more or all of the protecting groups present in the compounds of formulae I to XIX in question to be removed or for one or more or all of the functional groups that are not to participate in the reaction, or that would interfere with the reaction, to be converted into protected groups by the introduction of suitable protecting groups (especially hydroxy-protecting groups and/or carboxy-protecting groups).

The protection of functional groups by such protecting groups, suitable reagents for their introduction, suitable protecting groups and reactions for their removal will be familiar to the person skilled in the art. Examples of suitable protecting groups can be found in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New.York 1999, in "The Peptides"; Volume 3 (editors: E. Gross and J. Meienhofer), Academic Press, London and New York 1981, in "Methoden der organischen Chemie", Houben-Weyl, 4$^{th}$ edition, Vol. 15/I, Georg Thieme Verlag, Stuttgart 1974, in H.-D. Jakubke and H. Jescheit, "Aminosäuren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974.

Suitable hydroxy-protecting groups are especially selected from those of the acyl or ester type, e.g. lower alkanoyl, such as formyl, acetyl or isobutyroyl, benzoylformyl, chloroacetyl, dichloroacetyl, trichloroacetyl, trifluoroacetyl, methoxyacetyl, phenoxyacetyl, phenylacetyl, p-phenylacetyl, diphenylacetyl, 2,6-dichloro-4-methylphenoxyacetyl, 2,6-dichloro-4-(1,1,3,3-tetramethylbutyl)phenoxyacetyl, 2,4-bis(1,1-dimethylpropyl)phenoxyacetyl, chlorodiphenylacetyl, 3-phenylpropionyl, 4-azidobutyroyl, 4-methylthiomethoxybutyroyl, (E)-2-methyl-2-butenoyl, 4-nitro-4-methylpentanoyl, 4-pentenoyl, 4-oxopentanoyl, 4,4-(ethylenedithio)-pentanoyl, 5-[3-bis(4-methoxyphenyl) hydroxymethylphenoxy)laevulinyl, pivaloyl, crotonoyl, monosuccinoyl, benzoyl, p-phenylbenzoyl, 2,4,6-trimethylbenzoyl, 2-(methylthiomethoxymethyl)benzoyl, 2-(chloroacetoxymethyl)benzoyl, 2-[(2-chloroacetoxy)ethyl]benzoyl, 2-[(2-benzyloxy)ethyl]benzoyl, 2-[2-(4-methoxybenzyloxy)ethyl]benzoyl, 2-iodobenzoyl, o-(di-bromomethyl)benzoyl, o-(methoxycarbonyl)benzoyl, 2-chlorobenzoyl, 4-bromobenzoyl, 4-nitrobenzoyl, alkoxycarbonyl, such as methoxycarbonyl, ethoxycarbonyl, isobutoxycarbonyl, methoxymethylcarbonyl, 9-fluorenylmethoxycarbonyl, 2,2,2-trichloroethoxycarbonyl, 1,1-dimethyl-2,2,2-trichloroethoxycarbonyl, 2-(trimethylsilyl)ethoxycarbonyl, 2-(phenylsulfonyl)-ethoxycarbonyl, 2-(triphenylphosphonio)ethoxycarbonyl, vinyloxycarbonyl, allyloxycarbonyl, p-nitrophenoxycarbonyl, benzyloxycarbonyl, p-methoxybenzyloxycarbonyl, 3,4-dimethoxy-benzyloxycarbonyl, o-nitrobenzyloxycarbonyl, p-nitrobenzyloxycarbonyl, dansylethoxycarbonyl, 2-(4-nitrophenyl)ethoxycarbonyl, 2-(2,4-dinitrophenyl)ethoxycarbonyl, 2-cyano-1-phenylethoxycarbonyl, S-benzylthiocarbonyl, 4-ethoxy-1-naphthyloxycarbonyl, 3',5'-dimethoxybenzoinyloxycarbonyl, 2-methylthiomethoxyethoxycarbonyl, N-phenylcarbamoyl, dimethylethylphosphinothiolyl, methyldithiocarbonyl; N,N,N',N'-tetramethylphosphorodiamidoyl, sulfonyl, methanesulfonyl, benzenesulfonyl, toluenesulfonyl, 2-[(4-nitrophenyl)-ethyl]sulfonyl, allylsulfonyl, 2-formylbenzenesulfonyl, nitroxy, or protecting groups of the ether type, such as methyl, substituted methyl, preferably lower alkoxymethyl, especially methoxymethyl (MOM), methylthiomethyl, (phenyldimethylsilyl)methoxymethyl, benzyloxy-methyl, p-methoxybenzyloxymethyl, p-nitrobenzyloxymethyl, guaiacolmethyl, tert-butoxy-methyl, 4-pentenyloxymethyl, silyloxymethyl, lower alkoxy-lower alkoxymethyl, especially 2-methoxyethoxymethyl (MEM), 2,2,2-trichloroethoxymethyl, 2-(trimethylsilyl)-ethoxymethyl or methoxymethyl, tetrahydropyranyl, 3-bromotetrahydropyranyl, tetrahydrothiopyranyl, 4-methoxythiopyranyl, 1-methoxycyclohexyl, 4-methoxytetrahydrothiopyranyl, S,S-dioxy-4-methoxytetrahydrothiopyranyl, 1-[(2-chloro-4-methyl)phenyl]-4-methoxypiperidin-4-yl, 1-(2-fluorophenyl)-4-methoxypiperidin-4-yl, 1,4-dioxan-2-yl, tetrahydrofuranyl, tetrahydrothio-furanyl, 2,3,3a,4,5,6,7,7a-octahydro-7,8,8-trimethyl-4,7-methanobenzofuran-2-yl; substituted ethyl, such as 1-ethoxyethyl, 1-(2-chloroethoxy)ethyl, 1-[2-(trimethylsilyl)ethoxy]ethyl, 1-methyl-1-methoxyethyl, 1-methyl-1-benzyloxyethyl, 1-methyl-1-benzyloxy-2-fluoroethyl, 1-methyl-1-phenoxyethyl, 2,2,2-trichloroethyl, 1,1-dianisyl-2,2,2-trichloroethyl, 1,1,1,3,3,3-hexafluoro-2-phenylisopropyl, 2-trimethylsilylethyl, 2-(benzylthio)ethyl, 2-(phenylselenyl)ethyl, tert-butyl; allyl or propargyl, substituted phenyl ethers, such as p-chlorophenyl, p-methoxyphenyl, p-nitrophenyl, 2,4-dinitrophenyl or 2,3,5,6-tetrafluoro-4-(trifluoromethyl)-phenyl, benzyl, substituted benzyl, such as p-methoxybenzyl, 3,4-dimethoxybenzyl, o-nitrobenzyl, p-nitrobenzyl, p-halobenzyl, e.g. p-bromobenzyl, 2,6-dichlorobenzyl, p-cyano-benzyl, p-phenylbenzyl, 2,6-difluorobenzyl, p-azidobenzyl, 4-azido-3-chlorobenzyl, 2-tri-fluoromethylbenzyl or p-(methylsulfinyl)benzyl, 2- or 4-picolyl, 3-methyl-2-picolyl, 2-quinolinylmethyl, 1-pyrenylmethyl, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy)phenyldiphenylmethyl, 4,4',4''-tris(4,5-dichlorophthalimidophenyl)methyl), 4,4',4''-tris(laevulinoyloxyphenyl)methyl, 4,4',4''-tris(benzoyloxyphenyl)methyl, 4,4'-dimethoxy-3''-[N-(imidazolyl-methyl)]trityl, 4,4'-dimethoxy-3''-[N-(imidazolylethyl)carbamoyl]trityl, 1,1-bis(4-methoxyphenyl)-1'-pyrenylmethyl, 4-(17-tetrahydrobenzo[a,c,g,i]fluorenylmethyl)-4',4''-dimethoxytrityl, 9-anthryl, 9-(9-phenyl)xanthenyl, 9-(9-phenyl-10-oxo)anthryl, 1,3-benzodithiolan-2-yl, S,S-dioxo-benzoisothiazolyl; of the silyl ether-type, such as tri-lower alkylsilyl, e.g. trimethylsilyl, triethylsilyl, triisopropylsilyl, dimethylisopropylsilyl, diethylisopropylsilyl, dimethylthexylsilyl, tert-butyldimethylsilyl or di-tert-butylmethylsilyl, tert-butyldiphenylsilyl, triphenylsilyl, diphenylmethylsilyl, tris(trimethylsilyl)silyl, (2-hydroxystyryl)dimethylsilyl, (2-hydroxystyryl)-diisopropylsilyl, tert-butylmethoxyphenylsilyl or tert-butoxydiphenylsilyl.

Bridging protecting groups can likewise be used where a molecule contains two hydroxy groups (for example bridging hydroxy-protecting groups formed by $R_a$ and $R_c$ or $R_a'$ and $R_c'$ together) or a hydroxy-protecting group and a carboxy group (for example bridging protecting groups formed by $R_a$ and $R_b$ or $R_a'$ and $R_b$ in the molecules of the corresponding formulae mentioned hereinabove and hereinbelow in which those radicals are present).

A bridging hydroxy-protecting group (especially one formed by $R_a'$ and $R_c'$) is preferably selected from methylene, ethylidene, tert-butylmethylidene, 1-tert-butylethylidene, 1-phenylethylidene, 1-(4-methoxyphenyl)ethylidene, 2,2,2-trichloroethylidene, vinylmethylidene, cyclopentylidene, cyclohexylidene, cycloheptylidene, benzylidene, p-methoxybenzylidene, 2,4-dimethoxybenzylidene, 3,4-dimethoxybenzylidene, 2-nitrobenzylidene, 4-nitrobenzylidene, mesitylene, phenyl-(1,2-bis(methylenyl)), methoxymethylene, ethoxymethylene, dialkylsilylene, such as tert-butylsilylene, 1,3-(1,1,3,3-tetraisopropyldisiloxanylidene), 1,1,3,3-tetra-tert-butoxydisiloxanylidene), —C(=O)—, ethylboronyl (—(H₃C—CH₂)B—), phenylboronyl (-(phenyl)B—), o-acetamidophenylboronyl or especially isopropylidene.

Carboxy-protecting groups are especially ester-forming, enzymatically and/or chemically removable protecting groups, preferably enzymatically and/or chemically removable protecting groups, such as heptyl, 2-N-(morpholino)ethyl, cholinyl, methoxyethoxyethyl or methoxyethyl; or those which are primarily chemically removable, e.g. alkyl, such as lower alkyl, especially methyl, ethyl, substituted lower alkyl (except for benzyl and substituted benzyl), such as substituted methyl, especially 9-fluorenylmethyl, methoxymethyl, methoxy-ethoxymethyl, methylthiomethyl, 2-(trimethylsilyl)ethoxymethyl, benzyloxymethyl, pivaloyloxy-methyl, phenylacetoxymethyl, triisopropylsilylmethyl, 1,3-dithianyl-2-methyl, dicyclopropylmethyl, acetonyl, phenacyl, p-bromophenacyl, α-methylphenacyl, p-methoxyphenacyl, desyl, carbamidomethyl, p-azobenzenecarboxamidomethyl, N-phthalimidomethyl or 4-picolyl, 2-substituted ethyl, especially 2-iodo-, 2-bromo- or 2-chloro-ethyl, 2,2,2-trichloroethyl, 2-(trimethylsilyl)ethyl, 2-methylthioethyl, 2-(p-nitrophenylsulfenyl)ethyl, 2-(p-toluenesulfonyl)- ethyl, 2-(2'-pyridyl)ethyl, 2-(p-methoxyphenyl)ethyl, 2-(diphenylphosphino)ethyl, 1-methyl-1-phenylethyl, 2-(4-acetyl-2-nitrophenyl)ethyl or 2-cyanoethyl, tert-butyl, 3-methyl-3-pentyl, 2,4-dimethyl-3-pentyl or ω-chloro-lower alkyl, especially 4-chlorobutyl or 5-chloropentyl, cyclopentyl, cyclohexyl, lower alkenyl, especially allyl, methallyl, 2-methylbut-3-en-2-yl, 3-methylbut-2-enyl or 3-buten-1-yl, substituted lower alkenyl, especially 4-(trimethylsilyl)-2-buten-1-yl, cinnamyl or α-methylcinnamyl, lower alkynyl, such as prop-2-ynyl, phenyl, substituted phenyl, especially 2,6-dialkylphenyl, such as 2,6-dimethylphenyl, 2,6-diisopropyl-phenyl, 2,6-di-tert-butyl-4-methylphenyl, 2,6-di-tert-butyl-4-methoxyphenyl, p-(methylthio)-phenyl or pentafluorophenyl, benzyl, substituted benzyl, especially triphenylmethyl, diphenyl-methyl, bis(o-nitrophenyl)methyl, 9-anthrylmethyl, 2-(9,10-dioxo)anthrylmethyl, 5-dibenzo-suberyl, 1-pyrenylmethyl, 2-(trifluoromethyl)-6-chromonylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, 4-azidomethoxybenzyl, 4-{N-[1-(4,4-dimethyl-2,6-dioxo-cyclohexylidene)-3-methylbutyl]amino}benzyl, piperonyl or p-polymer-benzyl, tetrahydro-pyranyl, tetrahydrofuranyl, or silyl radicals, such as tri-lower alkylsilyl, especially trimethylsilyl, triethylsilyl, tert-butyldimethylsilyl, isopropyldimethylsilyl or di-tert-butylmethylsilyl, or phenyl-di-lower alkylsilyl, such as phenyldimethylsilyl; alternatively a carboxy group can also be protected in the form an oxazolyl, 2-alkyl-1,3-oxazolinyl, 4-alkyl-5-oxo-1,3-oxazolidinyl or 2,2-bistrifluoromethyl-4-alkyl-5-oxo-1,3-oxazolidinyl radical.

Amide-protecting groups are especially allyl, tert-butyl, N-methoxy, N-benzoyloxy, N-methyl-thio, triphenylmethylthio, tert-butyldimethylsilyl, triisopropylsilyl, 4-(methoxymethoxy)phenyl, 2-methoxy-1-naphthyl, 9-fluorenyl, tert-butoxycarbonyl, N-benzyloxycarbonyl, N-methoxy- or N-ethoxy-carbonyl, toluenesulfonyl, N-buten-1-yl, 2-methoxycarbonylvinyl, or especially alkyl, such as lower alkyl, or more especially substituted alkyl, especially benzyl, benzyl substituted by one or more radicals selected from lower alkoxy, such as methoxy, lower alkanoyloxy, such as acetoxy, lower alkylsulfinyl, such as methylsulfinyl, dicyclopropylmethyl, methoxymethyl, methylthiomethyl and N-benzoyloxymethyl; or bis(trimethylsilyl)methyl, trichloroethoxymethyl, tert-butyldimethylsilyloxymethyl, pivaloyloxymethyl, cyanomethyl, benzyl, 4-methoxybenzyl, 2,4-dimethoxybenzyl, 3,4-dimethoxybenzyl, 2-acetoxy-4-methoxy-benzyl, o-nitrobenzyl, bis(4-methoxyphenyl)phenylmethyl, bis(4-methylsulfinylphenyl)methyl, pyrrolidinomethyl, diethoxymethyl, 1-methoxy-2,2-dimethylpropyl or 2-(4-methylsulfonyl)ethyl.

It is characteristic of protecting groups that they are simple to remove (that is to say without undesirable secondary reactions taking place), for example by solvolysis, reduction, photo-lysis or alternatively under conditions analogous to physiological conditions, for example enzymatically.

The person skilled in the art will know which protecting groups can be used for which reactions and compounds of the present invention. Hydroxy-protecting groups $R_a$ and $R_a'$ are especially those which can be selectively introduced and removed, more especially those which are not removed during the conversion of compounds of formula XII. Here it is especially advisable to use hydroxy-protecting groups that do not contain too strongly electronegative substituents, more especially lower alkanoyl, such as acetyl, lower alkoxy-lower alkanoyl, such as methoxyacetyl, or protecting groups of the substituted methyl type, especially lower alkoxymethyl, more especially methoxymethyl (MOM), or lower alkoxy-lower alkoxymethyl, especially 2-methoxyethoxymethyl (MEM).

Acyloxy in formula I is especially the radical of an organic carboxylic or sulfonic acid having from 1 to 24 carbon atoms, unsubstituted or substituted by one or more radicals, especially from 1 to 3 radicals, preferably selected from lower alkoxy, halogen, nitro, lower alkoxycarbonyl, phenyl, phenyl-lower alkyl, phenyloxy, lower alkanoyloxy, benzoyloxy, di-lower alkyl-amino, N-phenyl-lower alkyl-N-lower alkyl-amino, N,N-di(phenyl-lower alkyl)-amino, carbamoyl, thiocarbamoyl, sulfamoyl and cyano, and saturated or partially or fully unsaturated, and is preferably the radical of an alkanecarboxylic acid or haloalkane-carboxylic acid, especially lower alkanoyl, of an arylcarboxylic acid, especially benzoic acid, or halo-lower alkanesulfonyl, such as trifluoromethanesulfonyl; or, in the case of a compound of formula I, a radical of formula I'

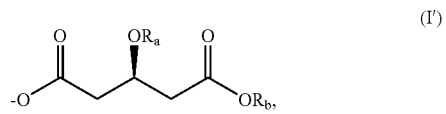

wherein $R_a$ and $R_b$ are as defined for compounds of formula I (the compound of formula I is then a symmetric anhydride (obtainable, for example, by reaction of the acid of formula I (OH instead of X) in the presence of a lower alkanecarboxylic acid anhydride, such as acetic anhydride, in the presence of catalytic amounts of acid)).

Activated hydrocarbyloxy or hydrocarbylthio is preferably unsubstituted or substituted lower alkyloxy, unsubstituted or substituted aryloxy (preferably having from 6 to 12 ring atoms) or unsubstituted or substituted heterocyclyloxy (preferably an unsaturated, fully or partially saturated mono- or bi-cyclic ring system having from 4 to 12 ring atoms and up to three hetero atoms selected from nitrogen, sulfur and oxygen) and is especially lower alkyloxy substituted in the 1-position by esterified carbonyl, such as lower alkoxycarbonyl, cyano or by phenylcarbonyl, especially lower alkoxycarbonyl-methoxy, such as ethoxycarbonyl-methoxy, cyanomethoxy or phenacyloxy (Ph-CO—CH$_2$—O—), tert-butylthio, N-benzotriazolyloxy, N-succinimidyloxy, pyridyloxy or pyridylthio, especially 2-pyridyloxy or more especially 2-pyridylthio, or electronegatively substituted aryloxy, such as p-nitrophenyloxy, 2,4-dinitro-phenyloxy; pentafluorophenyloxy or 2,4,5-trichlorophenyloxy.

Any hydroxy-protecting groups $R_a$ can then, if necessary, be removed selectively, especially by the methods described in the standard works mentioned above.

"Selectively" means especially enzymatically. In particular, lower alkanoyl, such as acetyl, is removed enzymatically, for example by esterases, such as pig's liver esterase, in suitable buffers, such as phosphate buffer, at preferred pH values of from 5 to 9, especially from 6 to 8. Further possible enzymes and reaction conditions will be found below under the definition of biocatalysts for the hydrolysis. Lower alkoxymethyl, such as MOM, or lower alkoxy-lower alkoxymethyl, such as MEM, is removed by chemical standard methods.

The diastereoselective reduction of a compound of formula XV (when $R_c'$ is a hydroxy-protecting group, after removal thereof) to form a compound of formula XVI in each case as defined above and below, is then preferably carried out in a chelate-controlled manner, there being used as chelate-forming agent preferably a di-lower alkyl borinic acid lower alkyl ester or mixtures of triethylborane or diethylborane methoxide with sodium borhydride, especially diethyl borinic acid ethyl ester. As solvent there are preferably used ethers, such as cyclic ethers, especially tetrahydrofuran, and/or alcohols, such as lower alkanols, e.g. methanol, or mixtures of them, preferred is a mixture of tetrahydrofuran and methanol; the preferred reaction temperatures being from −80 to −30° C., especially from −78 to 40° C.

Further, preferred is the diastereoselective reduction of compound of formula XV to XVI with hydrogen in the presence of a homogeneous metal catalyst. Customary, the reduction is carried out in the presence of an organic solvent. Preferred metal of the homogeneous metal catalyst is a metal of Group VII of the periodic table of elements. More preferred is a ruthenium catalyst, for the reaction with a ruthenium catalyst and hydrogen the preferred reaction temperatures being from 0 to 150° C. under pressure of 1 to 100 bar, preferably from 10 to 60° C. under pressure of 10 to 60 bar.

In addition, preferred is the diastereoselective reduction of compound of formula XV to XVI with hydrogen in the presence of an alkali metal salt or alkaline-earth metal salt and a heterogeneous platinum catalyst. Preferred salt is an alkaline-earth metal salt, most preferred is a magnesium salt, and especially preferred is magnesium acetate. Customary this diastereoselective reduction is carried under pressure between 1 to 100 bar at temperatures between 0 to 100° C. Most preferably the reduction is carried out using a platinum on carbon catalyst together with magnesium acetate with hydrogen under a pressure of 6 to 60 bar at temperatures between 10 to 60° C.

In a broader embodiment of the invention it is also preferred to use alternative reducing agents, such as sodium cyanoborohydride, but this results in lower diastereoselectivity and is therefore less preferred.

The bridging protecting group formed by $R_a'$ and $R_c'$ together, preferably as indicated above, especially the isopropylidene protecting group, is especially introduced by standard methods, preferably as described in the standard works mentioned above, in the case of the isopropylidene protecting group especially by reaction with acetone or, preferably, with a di-lower alkoxypropane, such as dimethoxypropane, in the presence of copper(II) sulfate, zinc chloride or, preferably, an acid, such as sulfuric acid or especially an organic sulfonic acid, such as an arylsulfonic acid (wherein aryl has especially from 6 to 10 ring atoms, e.g. naphthyl or phenyl, and is unsubstituted or mono- or poly-substituted, especially up to tri-substituted, especially by lower alkyl, such as methyl), preferably toluenesulfonic acid, or with a lower alkyl isopropenyl ether, such as ethyl isopropenyl ether, in the presence of an arylsulfonic acid. As preferred solvents there are used aprotic solvents, such as ethers, especially cyclic ethers, more especially tetrahydrofuran, or carboxylic acid amides, such as di-lower alkyl-lower alkanoylamides, e.g. dimethylformamide. The preferred reaction temperatures are in the range of from 0 to 80° C., especially from 20 to 30° C.

The reaction for the preparation of a compound of formula XI to form the corresponding compound of formula I is preferably effected under customary conditions, there being used as reagent for introducing a radical X especially an acid anhydride or an acid halide, preferably an inorganic acid halide, more especially a phosphorus trihalide, phosphorus pentahalide or thionyl halide, such as phosphoryl chloride, phosphoryl bromide, phosphorus trichloride, phosphorus tribromide, phosphorus pentachloride, phosphorus pentabromide, thionyl chloride or thionyl bromide, a symmetric anhydride of a lower alkanesulfonic acid halogenated at the α-carbon atom, such as trifluoromethanesulfonic anhydride, or an acid chloride or a symmetric anhydride of an organic carboxylic acid, especially an oxalyl halide, such as oxalyl chloride or bromide, the reaction being carried out in the absence or prefer-ably presence of a (preferably polar) solvent or solvent mixture, especially in a halogenated hydrocarbon, preferably methylene chloride, in the absence or presence of an acid amide, especially a di-lower alkyl-lower alkanoic acid amide, such as dimethylformamide, at preferred temperatures of from −20° C. to the reflux temperature of the reaction mixture in question, preferably from −10 to 50° C.

Hydrocarbyl $R_d$ in a compound of formula XII is preferably a saturated, fully or partially unsaturated, cyclic (having one or more, especially up to three, fused rings), linear, branched or mixed cyclic-linear or cyclic-branched hydrocarbon radical having up to 24 carbon atoms, preferably up to 10 carbon atoms, especially lower alkyl, and is unsubstituted or mono- or poly-substituted, preferably up to tri-substituted, especially by hydroxy, lower alkoxy, phenyl-lower alkoxy, lower alkanoyloxy, phenyl-lower alkanoyloxy, benzoyloxy, halogen, carboxy, lower alkoxycarbonyl or halo-lower alkyl, such as trifluoromethyl. Preference is given to lower alkyl, especially methyl or more especially ethyl, or lower alkoxy-lower alkyl, especially methoxymethyl. Preferably, in the compounds of formulae XIII and XIII the carboxy-protecting group $R_b$ is identical to the hydrocarbyl group $R_d$, especially in each case lower alkyl, more especially methyl or ethyl, branched lower alkyl or lower alkoxy-lower alkyl, especially methoxymethyl.

The preparation of a compound of formula XI is preferably effected with removal of the hydrocarbyl radical $R_d$ in the presence of an enantioselective catalyst, especially a biocatalyst.

As biocatalysts for the hydrolysis there are suitable cells or ruptured cells with the enzymes mentioned below, or especially enzymes as such, preferably esterases, lipases and proteases (peptidases or amidases, see U. T. Bornscheuer and R. T. Kazlauskas, in: Hydrolases in Organic Synthesis, Wiley-VCH, 1999, pages 65-195, ISBN 3-527-30104-6). Common representatives of those classes of enzyme are especially animal esterases (e.g. pig's liver esterase=PLE, pig's pancreas esterase=PPL), esterases from microorganisms or fungi (*B. subtilis* esterase, *Pichia* esterases, *yeast* esterases, *Rhizopus* sp. esterases (RML, ROL), *Penicillium* sp. esterases, *G. candidum* (GCL), *H. lanuginosa* (HLL), *Candida* sp. (CAL-A, CAL-B, CCL), *Aspergillus* sp. (ANL), *Pseudomonas* sp. (PCL, PFL) and the like), and also proteases, e.g. subtilisin, thermitase, chymotrypsin, thermolysin, papain, aminoacylases, penicillin amidases, trypsin or the like, to name only a few. The person skilled in the art will be familiar with further suitable enzymes, and the enzymes that can be used are not limited to those mentioned in the above list. Such enzymes can be obtained in the form of crude isolates and/or in purified form from natural sources and/or from recombinant microorganisms by means of modern cloning procedures via overexpression, amplification or the like. Commercially available enzymes are especially preferred. The enzymes can be present as such or immobilised or adsorbed on carriers, for example on silica gel, kieselguhr, such as Celite®, Eupergit® (Röhm & Haas, Darmstadt, Germany) or the like, or used in the form of "CLECs" (cross-linked enzymes), such as are available from ALTUS BIOLOGICS, the scope for use extending beyond the list given, as the person skilled in the art will know (see U. T. Bornscheuer and R. T. Kazlauskas, in: Hydrolases in Organic Synthesis, Wiley-VCH, 1999, pages 61-64, ISBN 3-527-30104-6; K. Faber in: Biotransformation in Organic Chemistry, Springer 1997, Third Edition, pages 345-357, ISBN 3-540-61688-8; H. J. Rehm, G. Reed in: Biotechnology, VCH 1998, Second Edition, pages 407-411). The enzymes can be used in pure organic solvents, e.g. liquid hydrocarbons, such as hexane, toluene or benzene, liquid ethers, such as diethyl ether, methyl tert-butyl ether or tetrahydrofuran, liquid halogenated hydrocarbons, such as methylene chloride, water or aqueous buffer solutions, in mixtures of those solvents, for example mixtures of one or more thereof with water or aqueous buffer solutions. The aqueous solution is preferably buffered, pH 5-9, it being possible to use customary buffer systems (see e.g. K. Faber in: Biotransformation in Organic Chemistry, Springer 1997, Third Edition, p. 305; or U. T. Bornscheuer and R. T. Kazlauskas, in: Hydrolases in Organic Synthesis, Wiley-VCH, 1999, pages 61-65). The pH is preferably kept substantially constant during the reaction. Most suitable for this purpose is an automatic titrator having a standardised acid or base solution, or manual titration. The reaction temperature is preferably in the range from 10 to 50° C., especially from 25 to 40° C. The amount of biocatalyst used and the concentrations of the reagents can be dependent upon the substrate and the reaction conditions (temperature, solvent etc.) selected in each case, as will be known to the person skilled in the art. There are preferably used commercially available enzymes (for example from Fluka, Sigma, Novo Nordisk, Amano, Roche and the like) or those listed in the current literature (see e.g. H.-J. Rehm, G. Reed in: Biotechnology, VCH 1998, $2^{nd}$ Edition, pages 40-42). Especially preferred for the preparation of enantiomerically pure compounds is α-chymotrypsin in phosphate buffer, especially at pH 7.0.

The preparation of an amide of formula I* from a compound of formula I is carried out under customary conditions for the introduction of ammonia or amines and, where applicable, amide-protecting groups. For example, for the introduction of —NH$_2$ (R*=R**=H) reaction with ammonia is carried out, preferably in a suitable solvent, such as an ether, e.g. a di-lower alkyl ether, such as tert-butyl methyl ether, at preferred temperatures of from −20 to 30° C., e.g. at 0° C. For the introduction of substituted alkyl radicals (especially R*=R**=benzyl), reaction with the corresponding amine (e.g. dibenzylamine) is carried out in the presence of a tertiary nitrogen base, such as a tri-lower alkylamine or pyridine, dimethylaminopyridine or the like, in a suitable solvent, such as a halogenated hydrocarbon, e.g. methylene chloride, at preferred temperatures of from −20 to 30° C., especially at approximately 0° C.

The introduction of protecting groups into compounds of formula XVI is carried out, if necessary, in accordance with standard methods, especially as described in the standard works mentioned.

The dehydration of a compound of formula I* wherein R* and R** are each hydrogen, $R_b'$ is a carboxy-protecting group and $R_c'$ is a hydroxy-protecting group is carried out in the presence of suitable dehydrating agents, such as phosphorus (V) oxide or phosphoryl chloride at elevated temperatures, or with cyanuric chloride, in an aprotic solvent, especially an ether, such as a lower alkane-lower alkyl ether, e.g. tert-butyl methyl ether, and/or an acid amide, especially an N,N-di-lower alkyl-lower alkanoylamide, such as dimethylformamide, at preferred temperatures of from 10° C. to the reflux temperature, for example from 20 to 30° C.

The reduction and removal of protecting groups from an amide compound of formula XVI for conversion into a compound of formula VI is carried out under standard conditions using suitable reducing agents, such as hydrogenating agents or hydrogen; for example by initial treatment with a hydride, such as borane, in a customary solvent, especially a solvent that stabilises the reducing agent, such as a cyclic ether, such as tetrahydrofuran, at preferred temperatures of from 0 to 60° C., especially from 30 to 50° C., and subsequent hydrogenation in the presence of a transition metal catalyst, especially a noble metal catalyst, such as platinum or palladium, in each case preferably bound to a carrier, especially carbon, in a suitable solvent, preferably an alcohol, such as ethanol, especially under normal pressure or elevated hydrogen pressure, for example at from 1 to 30 bar (especially for R* and R**=each benzyl).

Unless otherwise indicated, halogen is preferably fluorine, chlorine, bromine or iodine, more preferred is chlorine.

Wherever solvents are mentioned hereinabove and hereinbelow it is also possible, where expedient and possible, for mixtures of two or more of the mentioned solvents to be used. The person skilled in the art will know that for certain reactions such solvents or solvent mixtures must be used in anhydrous (absolute) form and that, if necessary, also the reaction vessels used must have dry surfaces.

Where necessary, the said reactions are carried out in the absence of oxygen, and often also in the absence of carbon dioxide and/or atmospheric moisture, for example under protective gas, such as argon or nitrogen.

Where possible, the starting compounds and intermediate compounds can also be used in the form of salts, obtained in the form of salts or converted into salts in accordance with customary processes, for example in the case of carboxy compounds into the corresponding metal salts, such as alkali metal salts, e.g. sodium or potassium salts, or alkaline earth metal salts, such as calcium salts, or salts with nitrogen bases, such as ammonium, tri-lower alkyl-ammonium, pyridinium salts or the like. Where salt formation is possible, any reference to any of the compounds should be understood as also including the corresponding salts.

In addition to the solvents already mentioned, it is also possible to use other suitable solvents, where expedient and possible for the reaction in question. Such solvents can be selected, for example, from the following list: water, esters, e.g. lower alkyl-lower alkanoates, such as diethyl acetate, ethers, e.g. aliphatic ethers, such as diethyl ether, or cyclic ethers, such as dioxane or tetrahydrofuran, liquid aromatic hydrocarbons, such as benzene or toluene, alcohols, such as methanol, ethanol or 1- or 2-propanol, nitriles, such as acetonitrile, halogenated hydrocarbons, such as dichloromethane, chloroform or ethylene chloride, acid amides, such as dimethylformamide, bases, e.g. heterocyclic nitrogen bases, such as pyridine, carboxylic acids, such as lower alkanecarboxylic acids, e.g. acetic acid, carboxylic acid anhydrides, e.g. lower alkanoic acid anhydrides, e.g. acetic anhydride, cyclic, linear or branched hydrocarbons, such as cyclohexane, hexane or isopentane, or mixtures of such solvents or other solvents, e.g. aqueous solutions. Such solvents and solvent mixtures can also be used in working-up, e.g. by chromatography or partition. Any mention of solvents or eluants hereinabove and hereinbelow should be understood as including also mixtures of such solvents or eluants.

The other compounds, especially of formula XX, are known, can be prepared according to methods known per se and/or are commercially available.

PREFERRED EMBODIMENTS OF THE INVENTION

Preferred aspects of the invention can be found in the claims, which are incorporated herein by reference.

Hereinabove and hereinbelow, the radicals in compounds of the formulae of the present invention have the meanings given hereinabove and hereinbelow (especially the specific meanings mentioned for certain reaction variants or methods), and the reaction conditions are in each case as defined hereinabove or hereinbelow, preferably as the preferred reaction conditions:

Preference is given to a process for the preparation of statin derivatives which comprises the preparation of a compound of formula I, as defined hereinabove and hereinbelow, from a compound of formula XI, preferably such a process for the preparation of a compound of formula I; the compound of formula XI in turn preferably being prepared from a compound of formula XII which, in turn, is preferably prepared from a compound of formula XIII.

Preference is given to a process for the preparation of statin derivatives, especially of formula VI, comprising initially the conversion of the compound of formula I into a compound of formula I*; then preferably reaction thereof with a compound of formula XX to form a compound of formula XV; then preferably conversion thereof into a compound of formula XVI; and finally preferably reduction of the latter to form a compound of formula VI.

In all the preferred embodiments, if necessary one or more or all of the protecting groups present are removed or one or more or all of the functional groups that are not to participate in a reaction, or that would interfere with the reaction, are converted into protected groups by the introduction of suitable protecting groups (especially hydroxy-protecting groups and/or carboxy-protecting groups); and, where salt-forming groups are present and the reaction in question is not impaired, the compounds of the present invention may also be in salt form.

A further embodiment of the present invention concerns the use of the compounds and processes of any of the preceeding claims for the preparation of a compound of formula VI.

In addition, the present invention relates to the use of a compound of formula VI for the preparation of Atorvastatin®. Atorvastatin® is commercially available, such as from Warner-Lambert/Gödecke-Parke Davies/Pfizer.

Of the compounds, the invention relates especially to those of formulae I, I*, VI, XV and XVI as such, especially those in which the substituents correspond to the radicals indicated in the respective Examples.

Special preference is given to the compounds 1d, 1e, 11a, 11b, 11c, 12a, 13a, 13b and Bb mentioned in the Examples, especially each individual compound.

The present invention relates especially to the reaction steps and new intermediate compounds mentioned in the following Examples.

EXAMPLES

The following Examples serve to illustrate the invention but do not limit the scope thereof.

Abbreviations Used:
Celite Celite®, filtration aid based on kieselguhr, trade mark of Celite Corp., USA
TLC thin-layer chromatography
DMF dimethylformamide
eq. equivalent
h hour(s)
Hünig's base N-ethyldiisopropylamine
min minute(s)
NMR nuclear magnetic resonance spectroscopy
PLE pig's liver esterase
m.p. melting point (° C.)
THF tetrahydrofuran
torr unit of pressure (mm mercury column); 1 torr corresponds to 0.1333 kPa Unless otherwise indicated, the ratios of the components of eluant mixtures, solvent mixtures and the like are given in parts by volume (v/v).

Reaction Scheme I for Examples 1 to 4

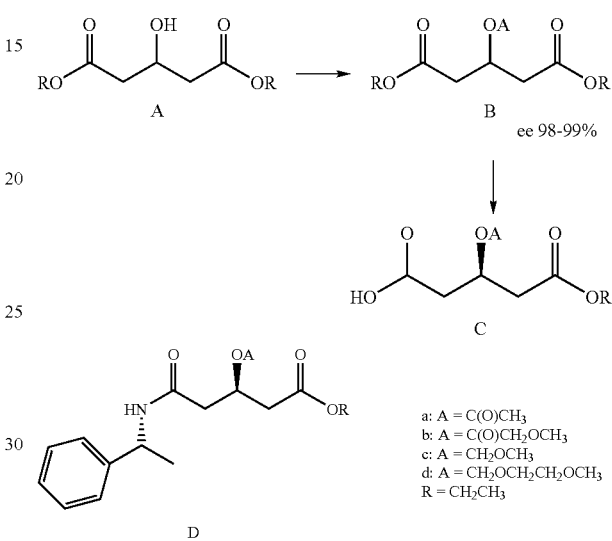

Example 1 a) Precursor of formula Ba wherein R=ethyl, A=acetyl(diethyl-3-acetoxyglutaric acid)

54.0 g of diethyl-3-hydroxyglutaric acid (Fluka, Buchs, Switzerland) are dissolved at room temperature in 26.5 ml of pyridine and 27.4 ml of acetic anhydride and the mixture is stirred for about 12 h until all the starting material has reacted. The mixture is diluted with ethyl acetate and washed in succession with water, 1N hydrochloric acid, saturated sodium hydrogen carbonate solution and saturated sodium chloride solution. The organic phase is separated and dried over magnesium sulfate. After evaporation of the organic solvent, 64.3 g of NMR-spectroscopically pure acetate, the title compound, remain: $^1$H-NMR (CDCl$_3$): 1.24 (t, 6H); 2.01 (s, 3H); 2.69 (d, 4H); 4.14 (q, 4H); 5.50 (quin., 1H).

b) Compound of formula Ca wherein R=ethyl, A=acetyl(monoethyl-3(R)-acetoxyglutaric acid)

160 g of diethyl-3-acetoxyglutaric acid Ba are suspended at room temperature in 570 ml of distilled water, and 168 ml of 0.1 M phosphate buffer (pH 7) are added. After the addition of 2.7 g of α-chymotrypsin (Sigma, Sigma Chemie, Buchs, Switzerland), the mixture is stirred vigorously and maintained at pH 7.8 using a pH meter and pH stat (Metrohm) and 0.5N sodium hydroxide solution. When the theoretical amount of hydroxide solution (1.3 liters) has been consumed, the mixture is extracted with ethyl acetate. The aqueous phase is adjusted to pH 1 with concentrated hydrochloric acid (conc.

HCl) and then extracted with ethyl acetate. Any cloudiness of the organic phase can be removed by filtration over Celite. After evaporation of the organic phase, 131 g (97%) of semi-ester Ca remain: $^1$H-NMR (CDCl$_3$): 1.25 (t, 3H); 2.03 (s, 3H); 2.71 (d, 2H); 2.77 (d, 2H); 4.14 (q, 2H); 5.50 (quin., 1H).

c) Determination of the enantiomeric excess (ee) of the monoacid Ca by means of the amide Da (R=ethyl, A=acetyl)

150 mg of the monoacid Ca are reacted in accordance with the customary methods of peptide coupling with 341 mg of (benzotriazol-1-yloxy)-tris(dimethylamino)phosphonium hexafluorophosphate, 246 mg of Hünig's base and 93 µl of R-phenylethylamine (Fluka, Buchs, Switzerland) in 1.5 ml of DMF at room temperature. After customary extraction, 188 mg of amide Da are obtained. NMR spectroscopy indicates a diastereoisomeric ratio of 99:1 on the basis of the shift difference between the two diastereoisomeric acetates and accordingly a ratio of R to S of 99:1. HPLC analysis (column: Chiracel OJ 25 cm×0.46 cm (Daicel Chemical Industries, Ltd., JP), n-hexane:ethanol=95:5, flow rate 1.2 ml/min, UV detection at 210 nm) confirms the ratio of R to S as 98.8:1.2. $^1$H-NMR (CDCl$_3$): 1.15 (t, 3H); 1.35 (d, 3H); 1.85 and 1.87 (2×s, total 3H, ratio as 99:1); 2.47 (m, 2H); 2.55 (dd, 1H); 2.65 (d, 1H); 4.01 (broad q, 1H); 5.00 (quint., 1H); 5.38 (m, 1H); 6.51 (broad d, NH); 7.20 (m, 5H).

Example 2 a) Precursor of formula Bb wherein R=ethyl, A=methoxyacetyl(diethyl-3-methoxy-acetoxyalutaric acid)

50.0 g of diethyl-3-hydroxyglutaric acid (Fluka, Buchs, Switzerland) are dissolved at 0° C. in 80 ml of dichloromethane; 20.6 ml of pyridine and 22.9 ml of methoxyacetyl chloride are added and the mixture is stirred at room temperature for about 12 h until all the starting material has reacted. The mixture is washed in succession with water, 1N hydrochloric acid, saturated sodium hydrogen carbonate solution and saturated sodium chloride solution. The organic phase is separated and dried over magnesium sulfate. After evaporation of the organic solvent, a dark-yellow syrup is obtained which is filtered over a small amount of silica gel using hexane/ethyl acetate (2:1). After evaporation of the solvent, 65.0 g of NMR-spectroscopically pure methoxyacetate Bb are obtained: $^1$H-NMR (CDCl$_3$): 1.20 (t, 3H); 2.65 (d, 4H); 3.35 (s, 3H); 3.90 (s, 2H); 4.04 (q, 4H); 5.55 (quin., 1H).

b) Compound of formula Cb wherein R=ethyl, A=methoxyacetyl(monoethyl-3(R)-methoxyacetoxy-glutaric acid)

40.0 g of diethyl-3-methoxyacetoxyglutaric acid Bb are suspended at room temperature in 150 ml of distilled water, and 43 ml of 0.1M phosphate buffer (pH 7) are added. After the addition of 0.4 g of α-chymotrypsin (Sigma; Sigma Chemie, Buchs, Switzerland), the mixture is stirred vigorously and maintained at pH 7.8 using a pH meter and pH stat (Metrohm) and 0.5N sodium hydroxide solution. After 18 h, a further 0.1 g of chymotrypsin is added and stirring is continued until the theoretical amount of hydroxide solution has been consumed. The mixture is then extracted with ethyl acetate (4×). The aqueous phase is adjusted to pH 1 with concentrated hydrochloric acid (conc. HCl) and then extracted with ethyl acetate. Any cloudiness of the organic phase can be removed by filtration over Celite. After evaporation of the organic phase, 24.8 g of semi-ester Cb remain: $^1$H-NMR (CDCl$_3$): 1.24 (t, 3H); 2.74 (d, 2H); 2.75 (d, 2H); 3.42 (s, 3H); 3.99 (s, 2H); 4.14 (q, 2H); 5.59 (quin., 1H).

Alternatively, immobilised chymotrypsin can also advantageously be used. It can be supported on silica gel (Sigma S0507, 230-400 mesh, average pore diameter 0.6 nm; Sigma Chemie, Buchs, Switzerland) by customary methods without loss of activity, easily removed and then used repeatedly.

c) Determination of the enantiomeric excess (ee) of the monoacid Cb by means of benzamide Db (R=ethyl, A=methoxyacetyl)

200 mg of the monoacid Cb are reacted by customary methods of peptide coupling with 392 mg of (benzotriazol-1-yloxy)-tris(dimethylamino)phosphonium hexafluorophosphate, 290 µl of Hünig's base and 88 µl of benzylamine (Fluka, Buchs, Switzerland) in 2.0 ml of DMF at room temperature. After customary extraction, 178 mg of amide Db are obtained. HPLC analysis (Chiracel OD 25 cm×0.46 cm (Daicel Chemical Industries, Ltd., JP), n-hexane:ethanol=9:1, flow rate 1 ml/min, UV detection at 210 nm) yields a ratio of R to S of 98.6:1.4. $^1$H-NMR (CDCl$_3$): 1.22 (t, I=7.0, 3H); 2.62 (d, I=6.5, 2H); 2.75 (dd, I=15.8, 5.3, 2H); 3.35 (s, 3H); 3.91 (s, 2H); 4.10 (q, I=7.0, 2H); 4.38 (d, I=5.9, 2H); 5.56-5.65 (m, 1H); 6.31 (t, br, NH); 7.21-7.33 (m, 5H).

d) Purification of the compound Cb wherein R=ethyl, A=methoxyacetyl(monoethyl-3(R)-methoxyacetoxyglutaric acid)

500 g of monoacid Cb are dissolved in 2 liters of tert-butyl methyl ether and heated to boiling. 400 ml (1 eq.) of dicyclohexylamine dissolved in 2 liters of tert-butyl methyl ether are added dropwise in the course of 10 min, followed by 4 liters of n-hexane. If crystallisation does not start spontaneously, seeding is carried out, followed by cooling to 5-10° C. The resulting crystals are filtered off with suction and dried in vacuo at 70° C. Yield: 694 g, 80% white crystals, m.p.=111° C. 3 g of the resulting salt are dissolved in 20 ml of water, NaCl is added to the solution and 1 eq. of 3N hydrochloric acid is added. The precipitated dicyclohexylamine hydrochloride is filtered off with suction and the clear filtrate is extracted repeatedly with tert-butyl methyl ether. After drying and removal of the solvent, 1.6 g, 92%, of monoacid Cb are obtained; ee≧99.5%, determined by way of the benzamide analogously to c).

Example 3 a) Precursor of formula Bc wherein R=ethyl, A=methoxymethyl(diethyl-3-methoxy-methoxaglutaric acid)

97.2 g of diethyl-3-hydroxyglutaric acid A (Fluka) are dissolved at 0° C. together with 210 ml of formaldehyde dimethylacetal in 350 ml of dichloromethane, and 61.3 g of phosphorus pentoxide are added in portions. The mixture is stirred vigorously overnight, the temperature of the mixture rising to room temperature. When conversion is complete (TLC monitoring), the mixture is decanted off, diluted with methylene chloride and washed in succession with 2× saturated sodium hydrogen carbonate solution and saturated sodium chloride solution. The organic phase is separated and dried over magnesium sulfate. After evaporation of the solvent, a colourless fluid is obtained which is distilled at 98-101° C./0.17 torr. 104.8 g (89%) of a colourless fluid, the title compound, are obtained: $^1$H-NMR (CDCl$_3$): 1.15 (t, 3H); 2.53 (m, 4H); 3.24 (s, 3H); 4.05 (q, 4H); 4.30 (quin., 1H); 4.58 (s, 2H).

b) Compound of formula Cc wherein R=ethyl, A=methoxymethyl(monoethyl-3(R)-methoxymethoxyglutaric acid)

7.4 g of diethyl-3-methoxymethoxyglutaric acid Bc are suspended at room temperature in 100 ml of distilled water, and 20 ml of 0.1M phosphate buffer (pH 7) are added. After the addition of 1.0 g of chymotrypsin, the mixture is stirred vigorously and maintained at pH 7.8 using a pH meter and pH stat (Metrohm) and 0.5N sodium hydrogen carbonate solution. When the theoretical amount of carbonate solution has been consumed, the mixture is extracted with ethyl acetate. The aqueous phase is adjusted to pH 3-3.5 with 0.5N hydrochloric acid and then extracted with ethyl acetate. Any cloudiness of the organic phase can be removed by filtration over Celite. After washing of the organic phase with saturated sodium chloride solution and evaporation of the organic phase, 5.4 g (82%) of spectroscopically clean monoacid, the title compound, remain: $^1$H-NMR (CDCl$_3$): 1.24 (t, 3H); 2.69 (m, 4H); 3.34 (s, 3H); 4.13 (q, 2H); 4.38 (quin., 1H); 4.68 (s, 2H).

c) Determination of the enantiomeric excess (ee) of the monoacid Cc by means of the amide with benzylamine 400 mg of the monoacid are reacted by customary methods for peptide coupling with 760 mg of (benzotriazolyl-1-yloxy)-tris(dimethylamino)phosphonium hexafluorophosphate, 215 µl of Hünig's base and 0.70 ml of benzylamine (Fluka) in 2.0 ml of DMF at from 0° C. to room temperature. After customary extraction, 567 mg of amide are obtained. HPLC analysis (Chiralcel OD, 25×0.46 cm, n-hexane:ethanol=98:2, 1 ml/min) confirms a ratio of R to S of more than 98:2. $^1$H-NMR (CDCl$_3$): 1.19 (t, 3H); 2.48 (dd, 2H); 2.56 (dd, 1H); 3.24 (s, 2H); 4.06 (broad q, 1H); 4.34 (m, 3H); 4.59 (m, 2H); 7.00 (broad s, NH); 7.20 (m, 5H).

Example 4 a) Precursor of formula Bd wherein R=ethyl, A=2-methoxyethoxymethyl(diethyl-3-(2-methoxyethyl)-oxymethoxyglutaric acid)

At 0° C., 11.23 g of diethyl-3-hydroxyglutaric acid A (Fluka) are introduced together with 11.8 ml of diisopropylethylamine into 40 ml of dichloromethane, and 8.6 g of 2-methoxy-ethoxymethyl chloride (Fluka) are added. The mixture is stirred vigorously overnight, the temperature of the mixture rising to room temperature. The mixture is diluted with methylene chloride and washed in succession with 2×1N hydrochloric acid, 2× saturated sodium hydrogen carbonate solution and saturated sodium chloride solution. The organic phase is separated and dried over magnesium sulfate. After evaporation of the solvent, a colourless liquid is obtained, 15.91 g (99%), the title compound. $^1$H-NMR (CDCl$_3$): 1.20 (t, 3H); 2.59 (m, 4H); 3.32 (s, 3H); 3.49 (m, 2H); 3.63 (m, 2H); 4.09 (q, 4H); 4.36 (quin., 1H); 4.73 (s, 2H).

b) Compound of formula Cd wherein R=ethyl, A=2-methoxyethoxymethyl(monoethyl-3(R)-(2-methoxyethyl)-oxymethoxyglutaric acid)

7.4 g of diethyl-3-(2-methoxyethyl)-oxymethoxyglutaric acid Bd are suspended at room temperature in 30 ml of distilled water, and 3.3 ml of 0.1M phosphate buffer (pH 7) are added. After the addition of 0.1 g of chymotrypsin, the mixture is stirred vigorously and maintained at pH 7.8 using a pH meter and pH stat (Metrohm) and 0.5N sodium hydroxide solution. When the theoretical amount of hydroxide solution has been consumed, the mixture is extracted with ethyl acetate. The aqueous phase is adjusted to pH 3-3.5 with 0.5N hydrochloric acid and then extracted with ethyl acetate. Any cloudiness of the organic phase can be removed by filtration over Celite. After washing of the organic phase with saturated sodium chloride solution and evaporation of the organic phase, 1.44 g (79%) of spectroscopically clean monoacid, the title compound, remain: $^1$H-NMR (CDCl$_3$): 1.25 (t, 3H); 2.02 (s, 3H); 2.67 (m, 4H); 3.38 (s, 3H); 3.55 (m, 2H); 3.69 (m, 2H); 4.12 (q, 4H); 4.41 (quin., 1H); 4.79 (q, 2H).

c) Determination of the enantiomeric excess (ee) of the monoacid Cc by means of the amide Dc ((R=ethyl, A=2-methoxyethoxymethyl)

380 mg of the monoacid Cd are reacted in accordance with customary methods for peptide coupling with 682 mg of (benzotriazolyl-1-yloxy)-tris(dimethylamino)phosphonium hexa-fluorophosphate, 493 µl of Hünig's base and 185 µl of R-phenylethylamine (Fluka) in 3.0 ml of DMF at from 0° C. to room temperature. After customary extraction, 403 mg of amide are obtained. NMR-spectroscopy indicates a diastereoisomeric ratio of greater than 95:5 on the basis of the shift difference between the two methoxy groups in the diastereoisomers. HPLC analysis (Chiralcel OD, 25×0.46 cm, n-hexane:ethanol=95:5, 1 ml/min) confirms the ratio of R to S as 98:2. $^1$H-NMR (CDCl$_3$): 1.22 (t, 3H), 1.45 (d, 3H); 2.48 (m, 2H); 2.62 (m, 2H); 3.30 (s, ca. 5%); 3.38 (s, 95%); 3.50 (m, 4H); 4.12 (1, 1H); 4.34 (quint., 1H); 4.79 (q, 2H); 5.11 (quint., 1H); 6.54 (broad d, NH), 7.34 (m, 5H).

Reaction Scheme II for Examples 5 and 7

The Radicals Being as Defined in the Examples

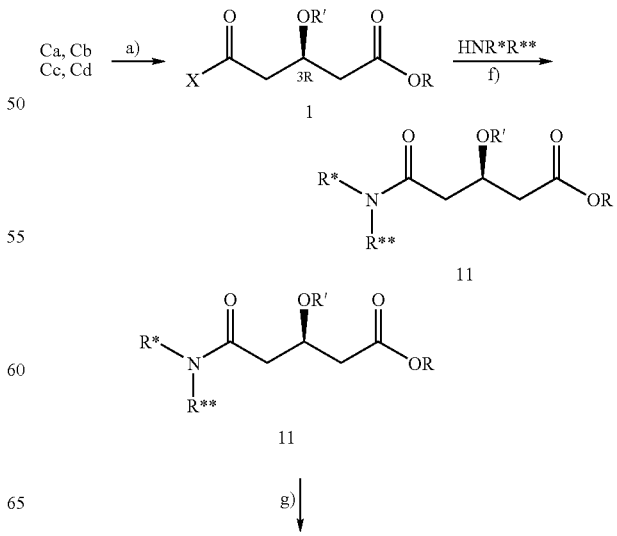

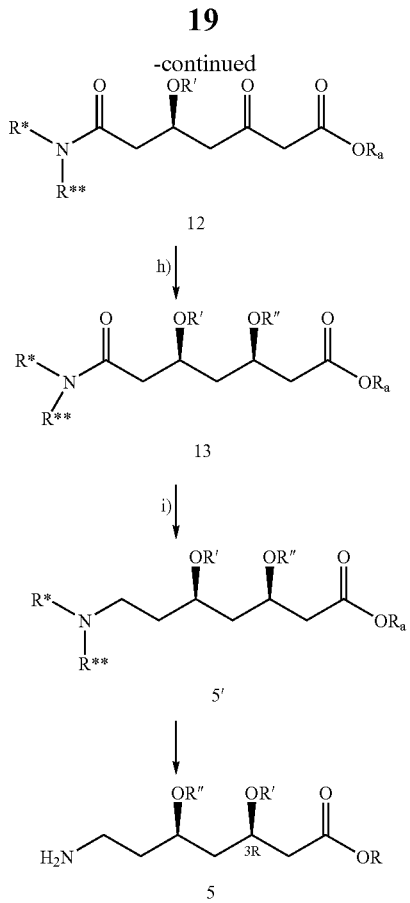

Example 5

Glutaric Acid Semihalides of Formula 1 a) Monoethyl ester of (3R)-acetoxy-glutaric acid chloride 1a (R=ethyl, X=Cl, R'=acetyl)

30.0 g of (3R)-acetoxyglutaric acid monoethyl ester (Ca) are dissolved in 60 ml of dry dichloromethane to which 20 drops of dry DMF have been added, and at 0-5° C. the solution is slowly treated with 21.9 g of oxalyl chloride. The mixture is then stirred for about 30 min. at 0° C. and then for a further 1.5 h at room temperature until the evolution of gas can no longer be observed. After evaporation of the solvent, 32.6 g of NMR-spectroscopically pure acid chloride 1a remain. (Colourless product can be obtained after molecular distillation). $^1$H-NMR (CDCl$_3$): 1.25 (t, 3H); 2.04 (s, 3H); 2.66 (dd, 1H); 2.70 (dd, 1H); 3.30 (dd, 1H); 3.34 (dd, 1H); 4.16 (q, 2H); 5.47 (m, 1H).

b) Monoethyl ester of (3R)-acetoxyglutaric acid bromide 1b (R=ethyl, X=Br, R'=acetyl)

5.0 g of (3R)-acetoxyglutaric acid monoethyl ester (Ca) are dissolved in 18 ml of dry dichloromethane to which a drop of dry DMF has been added, and at 0-5° C. the solution is slowly treated with 6.7 g of oxalyl bromide. The mixture is then stirred for about 30 min. at 0° C. and then for a further 2 h at room temperature until the evolution of gas can no longer be observed. After evaporation of the solvent, 6.6 g (98%) of spectroscopically pure acid bromide 1b remain: $^1$H-NMR (CDCl$_3$): 1.21 (t, 3H); 2.00 (s, 3H); 2.62 (dd, 1H); 3.39 (dd, 1H); 3.42 (dd, 1H); 4.11 (q, 2H); 5.41 (m, 1H).

c) Monoethyl ester of (3R)-methoxyacetoxyglutaric acid chloride 1c (R=ethyl, X=Cl, R'=methoxyacetyl)

21.0 g of monoethyl-3(R)-methoxyacetoxyglutaric acid Cb are dissolved in 100 ml of dry dichloromethane to which 40 µl of dry DMF has been added, and at 0-5° C. the solution is slowly treated with 13.9 g of oxalyl chloride. The mixture is then stirred for about 4 h, the temperature of the mixture rising to room temperature. The mixture is then diluted with ethyl acetate and extracted 3× with ice-water, and the organic phase is dried over sodium sulfate. After evaporation of the solvent, 20.9 g of NMR-spectroscopically pure acid chloride 1c remain: $^1$H-NMR (CDCl$_3$): 1.20 (t, 3H); 2.04 (s, 3H); 2.67 (m, 2H); 3.32 (m, 2H); 3.36 (s, 3H); 3.95 (s, 2H); 4.09 (q, 2H); 5.52 (m, 1H).

d) Monoethyl ester of (3R)-methoxymethoxyglutaric acid chloride 1d (R=ethyl, X=Cl, R'=methoxymethyl)

0.40 g of the monoacid Cc is dissolved in 2 ml of dry dichloromethane to which 3 drops of dry DMF are added, and at 0-5° C. the solution is slowly treated with 0.18 ml of oxalyl chloride until the evolution of gas can no longer be observed. After evaporation of the solvent, 0.43 g of acid chloride 1d remains: $^1$H-NMR (CDCl$_3$): 1.25 (t, 3H); 2.67 (m, 4H); 3.69 (s, 3H); 4.13 (q, 2H); 5.53 (q, 1H); 5.54 (s, 2H).

e) Monoethyl ester of (3R)-(2-methoxyethyl)-oxymethoxyglutaric acid chloride 1e (R=ethyl, X=Cl, R'=2-methoxyethyloxymethyl)

0.53 g of the monoacid Cd is dissolved in 2 ml of dry dichloromethane to which 2 drops of dry DMF have been added, and at 0-5° C. the solution is slowly treated with 0.21 ml of oxalyl chloride until the evolution of gas can no longer be observed. After evaporation of the solvent, 0.54 g of acid chloride 1e remains: $^1$H-NMR (CDCl$_3$): 1.21 (t, 3H); 2.55 (m, 1H); 2.65 (m, 1H); 3.24 (m, 2H); 3.34 (s, 3H); 3.50 (m, 2H); 3.65 (m, 2H); 4.10 (q, 2H); 4.38 (quint., 1H); 4.74 (m, 2H).

Example 6

Preparation of Compounds 11, 12, 13 and 5'

(i) (f) Preparation of 11a (R=ethyl, R'=acetyl, R*=H, R**=H)

50 g of (3R)-acetoxyglutaric acid monomethyl ester monochloride 1a are dissolved in 500 ml of tert-butyl methyl ether and at 0° C. treated with ammonia gas until the absorption of ammonia has ceased. The precipitated ammonium chloride is filtered off. After evaporation of the solvent, 44.5 g (97%) of NMR-spectroscopically pure amide 11a remain: $^1$H-NMR (CDCl$_3$): 1.24 (t, 3H); 2.02 (s, 3H); 2.60 (dd, 2H); 2.72 (m, 2H); 4.13 (q, 2H); 5.47 (m, 1H); 5.95 (s, br, 2H).

(ii) (f) Preparation of 11b (R=ethyl, R=acetyl, R*=benzyl, R**=benzyl)

At 0° C., a mixture of 41.7 g of dibenzylamine and 21.4 g of triethylamine is slowly added dropwise to 50 g of (3R)-acetoxyglutaric acid monomethyl ester monochloride 1a in 250 ml of methylene chloride and the mixture is stirred at room temperature for a further 2 h. The reaction mixture is then washed with 100 ml of 0.1N HCl and 2×100 ml of water and the organic phase is dried over sodium sulfate. After evaporation of the solvent, 79.8 g (95%) of NMR-spectroscopically pure dibenzylamide 2b remain: ¹H-NMR (CDCl₃): 1.24 (t, 3H); 1.99 (s, 3H); 2.72 (m, 2H), 2.90 (m, 2H); 4.13 (qq, 2H); 4.48 (q, 2H); 4.55 (q, 2H), 5.63 (m, 1H), 7.25 (m, 10H).

(iii) (f) Preparation of 11c (R=ethyl. R=H, R*=benzyl, R**=benzyl)

60 g of (3R)-acetoxyglutaric acid monoethyl ester mono (N,N-dibenzyl)amide 11b are stirred in 600 ml of 2M ethanolic HCl at room temperature for 12 h. After evaporation of the solvent, 53.1 g (99%) of NMR-spectroscopically pure dibenzylamide 11c remain: ¹H-NMR (CDCl₃): 1.24 (t, 3H); 2.60 (m, 2H); 2.90 (m, 2H); 4.10 (q, 2H); 4.43 (m, 2H), 4.50 (m, 1H), 4.55 (m, 2H), 7.25 (m, 10H).

(ix) (k) Preparation of 5'a (Ra=tert-butyl, R' and R" together=isopropylidene)

Starting from 13, the amine 5'a is prepared by reduction with hydrogen in the presence of ammonia and a molybdenum-doped Raney nickel catalyst in methanol (see Baumann, K. L., et al., Tetrahedron Lett. 33(17), 2283-2284 (1992)).

(x) (g) Preparation of 12a (Ra=tert-butyl, R'=H, R*=benzyl, R**=benzyl)

At −20° C., 500 ml of butyllithium (1.6M in hexane) are slowly added to 86.0 g of diisopropyl-amine in 200 ml of THF and the reaction mixture is stirred for a further 10 min. Then 92.8 g of tert-butyl acetate are slowly added and stirring is continued for a further hour at −20° C. A solution of 71 g of 11c in 150 ml of THF is then slowly added and the reaction mixture is stirred for a further 2 h at −20° C., then slowly heated to room temperature and stirred for a further 2 h. 500 ml of 4N hydrochloric acid are then slowly added and the phases are separated. The organic phase is washed with 2×250 ml of saturated sodium chloride solution and dried over sodium sulfate. After evaporation of the solvent, 85 g of crude dibenzylamine 12a remain: ¹H-NMR (CDCl₃): 1.46 (d,d, 9H); 2.55 (m, 2H); 3.39 (s, 2H); 4.42 (s, 2H); 4.54 (m, 1H); 4.58 (s, 2H); 7.25 (m, 10H).

(xi) (h) Preparation of the compound 13a (Ra=tert-butyl, R'=H, R"=H, R*=benzyl, R**=benzyl)

At −40° C., a solution of 18.6 g of 12a in 50 ml of THF is slowly added to a mixture of 130 ml of THF, 70 ml of methanol and 70 ml of triethylborane (1M in THF) and the reaction mixture is cooled to −70° C. 2.85 g of sodium borohydride are added in 5 portions and stirring is continued at −70° C. for a further 90 min. After the addition of 85 ml of 1M hydrochloric acid, the reaction mass is heated to room temperature. 100 ml of ethyl acetate and 10 g of sodium chloride are added and the phases are separated. The organic phase is dried with sodium sulfate and the solvent is evaporated off. The residue is 5× taken up in 100 ml of methanol and concentrated by evaporation. 17.7 g (95%) of crude syn-dihydroxy-dibenzylamide 13a remain: ¹H-NMR (CDCl₃): 1.46 (dd, 9H); 1.58 (m, 2H); 2.32 (m, 2H), 2.51 (m, 2H); 4.11 (m, 1H); 4.20 (m, 1H); 4.35 (m, 2H); 4.51 (q, 2H); 7.25 (m, 10H).

(xii) (Conversion according to h) Preparation of 13b (Ra=tert-butyl R' and R" together=isopropylidene, R*=benzyl, R**=benzyl)

17.0 g of crude 13a are dissolved in 50 ml of 2,2-dimethoxypropane. After the addition of 0.2 ml of HCl (4M in dioxane), the solution is stirred for 2 h at room temperature. Washing is then carried out with 50 ml of saturated sodium hydrogen carbonate solution and the organic phase is dried over sodium sulfate. After evaporation of the solvent, 18.3 g (98%) of NMR-spectroscopically pure acetonide 13b remain: ¹H-NMR (CDCl₃): 1.27 (s, 3H); 1.36 (s, 9H); 1.38 (m, 2H); 1.42 (s, 3H); 2.33 (m, 4H); 4.20 (m, 1H); 4.25 (dd, 2H); 4.44 (m, 1H); 4.67 (dd, 2H); 7.25 (m, 10H).

(xiii) (i) Preparation of the compound 5a (Ra=tert-butyl, R' and R" together=isopropylidene)

30 ml of borane in THF (1M) are added to a solution of 4.7 g of crude 13b in 20 ml of THF and stirring is carried out for 1 h at room temperature. The solution is then heated to 40° C. and stirred for a further 4 h. 20 ml of saturated sodium hydrogen carbonate solution is added to the reaction solution and extraction is then carried out with 20 ml of ethyl acetate. The organic phase is washed with 2×10 ml of water and dried over sodium sulfate. After evaporation of the solvent, the residue is taken up in 20 ml of ethanol and hydrogenated with 5% palladium on carbon at 55° C./20 bar. After the catalyst has been filtered off and the solvent evaporated, 1.8 g (67%) of crude amine 5a remain. The spectroscopic data correspond (except for the butyl radical Rₐ which differs) to those of compound 5a.

(xiv) (i) Preparation of the compound 5 (Rₐ=tert-butyl, R' and R" together=isopropylidene)

A solution of 1.52 kg of 13 in 2 lt diglyme was charged into a 5 l reactor. To this solution was added 246 g sodium borohydride. 0.78 l trimethyl silyl chloride was added slowly over a period of 1 hour. The reaction mixture was diluted with 1 lt hexane. The resulting reaction mixture was slowly poured into a mixture of 2 lt sodium hydrogene carbonate and 2 lt hexane. The reaction mixture was heated to reflux and stirred for an additional 2-3 hours. The reaction mixture was cooled to room temperature and the 2 phases were separated. The hexane phase was washed 4 times with 3 lt water and stirred for 1 hour with 0.1 kg active carbon. After filtration and evaporation of the solvent 1.3 kg of 5c

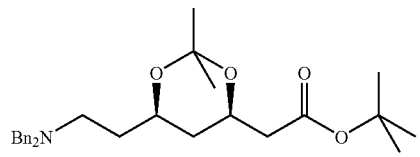

5c was obtained as a yellow oil and subsequently 1.3 kg of 5c charged in a 5 lt autoclave with 2.7 lt methanol and 0.3 lt water and purged with nitrogen. 62.5 g Pd—C were added and the autoclave was purged 3 times with hydrogen followed by hydrogenation of the reaction mixture at 10 bar at a temperature of 70° C. for 3 hours. The catalyst was removed by filtration and the solvent was removed in vacuum leaving a cloudy residue. This residue is poured into a well stirred suspension of 0.2 kg silica gel in 2.5 lt heptane. This suspension is filtered after 30 min and the filter cake is washed with heptane. This procedure gives 3.3 kg of a light yellow heptane solution, containing 460 gr 5a.

Example 7

Further Use of Compound 5 from Reaction Scheme II

For the preparation of atorvastatin, a compound 5 is reacted with a compound of formula 17

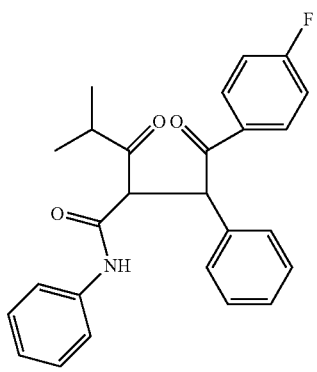

17 analogously to the conditions described in WO 89/07598 for the reaction between that compound and a compound of formula $H_2N-CH_2CH_2-CH(OR_{10})(OR_{11})$, wherein $R_{10}$ and $R_{11}$ are alkyl having up to 8 carbon atoms or together are 1,2-(1-methyl)ethylidene, 1,2-ethylidene or 1,3-propylidene. Subsequent removal of protecting groups and, if necessary, opening of the lactone ring yields atorvastatin.

Example 8 syn-Selective Hydrogenation of 6-Dibenzylcarbamoyl-5-hydroxy-3-oxo-hexanoic acid tert-butyl ester (use of compound 12 from Reaction scheme II)

950 g 6-Dibenzylcarbamoyl-5-hydroxy-3-oxo-hexanoic acid tert-butyl ester was dissolved in 3.8 l methanol and transferred into a 6.3 l steel autoclave. 285 g Pt/C (5%) wetted with 200 ml methanol and 71.25 g magnesium acetate were added and the autoclave was purged three times with nitrogen and three times with hydrogen. Hydrogenation was conducted at 25 bar and 35° C. for 18 h. After cooling to room temperature, the pressure was released, purged with nitrogen and the catalyst was filtered off and washed with 1 l methanol. Most of the solvent was distilled off, the residue was dissolved in 3 l ethylacetate and washed two times with 1 l water. The organic phase was evaporated to dryness.

Yield: 932 g 13a yellow oil (98%), with a syn/ant ratio of 7.6/1.

We claim:
1. A compound of formula XVI:

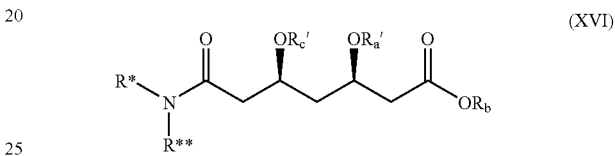

(XVI)

wherein $R_a'$ and $R_c'$ are each independently of the other hydrogen or a hydroxy-protecting group, or together are a bridging hydroxy-protecting group, R* and R** are hydrogen or phenyl-lower alkyl; and $R_b$ is a carboxy-protecting group.

2. The compound of claim 1, wherein $R_a'$ and $R_c'$ are each independently of the other hydrogen, lower alkanoyl, or lower alkoxy-lower alkanoyl; or together are an isopropylidene-protecting group; and wherein R* and R** are both hydrogen or benzyl; and $R_b$ is a lower-alkyl.

3. The compound of claim 2, wherein $R_a'$ and $R_c'$ are each independently of the other hydrogen, acetyl, or methoxyacetyl; and $R_b$ is tert-butyl.

* * * * *